(12) United States Patent
Slowey et al.

(10) Patent No.: US 8,252,268 B2
(45) Date of Patent: Aug. 28, 2012

(54) FORMOTEROL AND MOMETASONE AEROSOL FORMULATIONS

(75) Inventors: Alexander D. Slowey, Stapleford (GB); Susannah C. Boswell, Northants (GB); Philip A. Jinks, Loughborough (GB)

(73) Assignee: 3M Innovative Properties Company, St. Paul, MN (US)

( * ) Notice: Subject to any disclaimer, the term of this patent is extended or adjusted under 35 U.S.C. 154(b) by 926 days.

(21) Appl. No.: 10/509,184

(22) PCT Filed: Mar. 21, 2003

(86) PCT No.: PCT/US03/08710
§ 371 (c)(1),
(2), (4) Date: Sep. 24, 2004

(87) PCT Pub. No.: WO03/086350
PCT Pub. Date: Oct. 23, 2003

(65) Prior Publication Data
US 2005/0255049 A1   Nov. 17, 2005

(30) Foreign Application Priority Data

Apr. 5, 2002   (GB) .................................... 0207906.9

(51) Int. Cl.
*A61K 9/00*   (2006.01)
*A61K 9/10*   (2006.01)
*A61K 9/12*   (2006.01)

(52) U.S. Cl. .............................. 424/46; 424/45; 424/489

(58) Field of Classification Search .................. 424/489, 424/43, 45, 46; 128/200.14, 200.23
See application file for complete search history.

(56) References Cited

U.S. PATENT DOCUMENTS

| | | | |
|---|---|---|---|
| 4,472,393 A | 9/1984 | Shapiro | |
| 5,795,564 A | 8/1998 | Aberg et al. | |
| 6,129,905 A | 10/2000 | Cutie | |
| 6,131,566 A * | 10/2000 | Ashurst et al. | 128/200.14 |
| 6,264,923 B1 | 7/2001 | Oliver et al. | |
| 2004/0081627 A1* | 4/2004 | Jinks et al. | 424/46 |
| 2009/0246149 A1* | 10/2009 | Jinks et al. | 424/45 |

FOREIGN PATENT DOCUMENTS

| | | |
|---|---|---|
| EP | 0 057 401 A1 | 8/1982 |
| WO | WO 92/04365 * | 3/1992 |
| WO | WO 94/21228 | 9/1994 |
| WO | WO 94/21229 | 9/1994 |
| WO | WO 95/20393 | 8/1995 |
| WO | WO 97/47286 | 12/1997 |
| WO | WO 98/08519 | 3/1998 |
| WO | WO 98/21175 | 5/1998 |
| WO | WO 00/07567 | 2/2000 |
| WO | WO 00/51591 | 9/2000 |
| WO | WO 00/53187 * | 9/2000 |
| WO | WO 01/78740 * | 10/2001 |
| WO | WO 01/78744 | 10/2001 |
| WO | WO 02/11711 | 2/2002 |
| WO | WO 02/30394 A2 * | 4/2002 |
| WO | WO 03/020253 A2 | 3/2003 |
| WO | WO 2004/020289 | 3/2004 |

OTHER PUBLICATIONS

Seddon, K.R., "Pseudopolymorph: a polemic," Crystal Growth & Design, 2004, 4(6), pp. 1087, web release date Oct. 19, 2004.*
Braga et al. Chem. Commun., "Making Crystals from Crystals: a green route to crystal engineering and polymorphism," 2005, pp. 3635-3645.*
Vippagunta et al. "Crystalline Solids," Advanced Drug Delivery Reviews, 2001, 48, pp. 3-26.*

* cited by examiner

*Primary Examiner* — James H. Alstrum Acevedo

(57) ABSTRACT

A pharmaceutical aerosol formulation comprising particles of (a) formoterol or a pharmaceutically acceptable salt, solvate or physiologically functional derivative thereof and (b) mometasone or a pharmaceutically acceptable salt, solvate, or physiologically functional derivative thereof dispersed in a propellant selected from the group consisting of 1,1,1,2-tetrafluoroethane, 1,1,1,2,3,3,3-heptafluoropropane and a mixture thereof, and a bulking agent having a mass median diameter of less than one micron.

12 Claims, No Drawings

FORMOTEROL AND MOMETASONE AEROSOL FORMULATIONS

FIELD OF THE INVENTION

This invention relates to medicinal aerosol formulations and in particular to suspension aerosol formulations containing formoterol and mometasone and a nano-particulate auxiliary powder suitable for administration to the respiratory tract.

BACKGROUND

Formoterol, N-[2-hydroxy-5-(1-hydroxy-2-((2-(4-methoxyphenyl)-1-methylethyl) amino)ethyl)phenyl]formamide, particularly in the form of its fumarate salt, is a bronchodilator used in the treatment of inflammatory or obstructive airways diseases.

EP 057 401 and U.S. Pat. No. 4,472,393 describe mometasone i.e. 9,21-dichloro-11,17dihydroxy-16alpha-methylpregna-1,4-diene-3,20-dione, esters thereof such as mometasone furoate i.e. (11 beta, 16alpha)-9,21-dichloro-17-[(2-furanyl-carbonyl)oxy]-11-hydroxy-16-methylpregna-1,4-diene-3, 20-dione, and pharmaceutical formulations thereof. Mometasone is an antiinflammatory corticosteroid, which is now used clinically in the treatment of respiratory disorders.

WO 00/51591 describes medicaments and pharmaceutical compositions containing, separately or together, (A) formoterol or a pharmaceutically acceptable salt thereof or a solvate of formoterol or a solvate of said salt and (B) mometasone furoate, for simultaneous, sequential or separate administration in the treatment of an inflammatory or obstructive airways disease. As an example for a suspension aerosol formulation for a metered dose inhaler, WO 00/51591 discloses a composition consisting of 0.012% by weight formoterol fumarate dihydrate, 0.250% by weight mometasone furoate, 2.5% by weight ethanol, 60.768% by weight 1,1,1,2,3,3,3-heptafluoropropane (HFC 227) and 36.740% by weight 1,1, 1,2-tetrafluoroethane (HFC 134a).

WO 00/53187 discloses suspension aerosol formulations consisting of micronized formoterol fumarate dihydrate (6 µg), micronized mometasone furoate monohydrate (100 µg), oleic acid (0.005% based on propellant), ethanol (2% based on propellant) and HFC 134a (up to 25, 50 or 100 µl) as well as suspension formulations consisting of micronized formoterol fumarate dihydrate (12 µg), micronized mometasone furoate monohydrate (200 µg), oleic acid (0.01% based on propellant), ethanol (3% based on propellant) and HFC 227/HFC 134a (15/85, up to 25, 50 or 100 µl).

WO 01/78744 discloses suspension aerosol formulations consisting of micronized formoterol fumarate or the dihydrate thereof (6 to 24 µg per actuation), micronized mometasone furoate (100 or 200 µg per actuation) and HFC 134a.

An important aspect in formulating pharmaceutical compositions which have a micronized drug dispersed in a propellant is the homogeneity of the dispersed drug. The drug can sediment or cream depending on the density difference between drug and propellant, or it can flocculate, which requires some degree of agitation to deflocculate it. Inhomogeneity of the dispersed drug may in turn lead to delivery of incorrect doses when the formulation is dispensed from the metering valve. This aspect represents a challenge when formulating suspensions of a single drug, but is particularly challenging for a combination of drugs, like formoterol and mometasone, in which each drug has a significantly different potency and thus concentration in formulation. Furthermore, the densities of the two drugs differ appreciably, e.g. formoterol fumarate has a density of 1.3 g cm$^{-3}$, while mometasone furoate has a density of 1.4 g cm$^{-3}$.

SUMMARY OF THE INVENTION

We have found that the use of a particulate bulking agent having a mass median diameter of less than one micron in aerosol compositions comprising formoterol and mometasone dispersed in HFC 134a, HFC 227 or mixtures thereof, allows the provision of dispersions of both drugs showing desirably high physical stability and homogeneity.

The present invention provides a pharmaceutical aerosol formulation comprising particles of (a) formoterol or a pharmaceutically acceptable salt, solvate or physiologically functional derivative thereof and (b) mometasone or a pharmaceutically acceptable salt, solvate, or physiologically functional derivative thereof dispersed in propellant HFC 134a and/or HFC 227 and a bulking agent having a mass median diameter of less than one micron.

In particular, it has been found that the application of such a nano-sized bulking agent having a mass median diameter of less than one micron aids in minimizing the tendency of both formoterol and mometasone to cream or sediment, independent of the density difference of the respective drug to one another and to the propellant. More particularly, it has been found that the application of such a nano-sized bulking agent aids in maintaining a high sediment volume (i.e. minimizing a dense packing of the sediment) and/or the formation of a voluminous, loosely flocculated matrix, enhancing the re-dispersion and/or de-flocculation of the two drugs upon agitation.

The use of a particulate bulking agent having a mass median diameter of less than one micron in pharmaceutical aerosol formulations comprising a suspension of drug particles in a propellant is disclosed in commonly assigned co-pending application PCT US01/30575.

Formulations according to the invention are particularly suitable for use in inhalation therapy, in which a therapeutically effective amount of the formulation is delivered to the lung by oral or nasal inhalation, more particularly for prophylaxis or treatment of a clinical condition for which a selective $\beta_2$-adrenoreceptor agonist and/or antiinflammatory corticosteroid is indicated. The present invention also provides a method for the prophylaxis or treatment of a clinical condition in a mammal, such as a human, for which a selective $\beta_2$-adrenoreceptor agonist and/or antiinflammatory corticosteroid is indicated, which comprises administration via inhalation a therapeutically effective amount of the formulation as described above. In particular, the present invention provides such methods for the prophylaxis or treatment of a disease associated with reversible airways obstruction such as asthma, chronic obstructive pulmonary disease (COPD), respiratory tract infection or upper respiratory tract disease.

In another aspect of the present invention, there is provided a dispenser comprising an aerosol vial equipped with a dispensing valve containing a formulation as described above.

DETAILED DESCRIPTION

It is to be understood that the present invention covers all combinations of particular and preferred aspects of the invention described herein.

As would be appreciated by the skilled person, formoterol includes two asymmetric centres, and mometasone contains several asymmetric centres. The present invention includes each isomer of formoterol either in substantially pure form or admixed in any proportions or a racemic mixture, particularly the (R,R)-isomer as well as each isomer of mometasone either in substantially pure form or admixed in any proportions. The enantiomers of formoterol have been described previously, for example, in WO 98/21175 and U.S. Pat. No. 5,795,564.

By the term "physiologically functional derivative" is meant a chemical derivative of formoterol or mometasone having the same physiological function as the free compound, for example, by being convertible in the body thereto. According to the present invention, examples of physiologically functional derivatives include esters.

Suitable salts according to the invention include those formed with both organic and inorganic acids. Pharmaceutical acceptable acid addition salts include but are not limited to those formed from hydrochloric, hydrobromic, sulphuric, citric, tartaric, phosphoric, lactic, pyruvic, acetic, trifluoroacetic, succinic, oxalic, fumaric, maleic, oxaloacetic, methanesulphonic, ethanesulphonic, p-toluenesulphonic, benzenesulphonic, isethionic, and naphthalenecarboxylic, such as 1-hydroxy-2-naphthalenecarboxylic acids.

Pharmaceutically acceptable esters of formoterol or mometasone may have a hydroxyl group converted to a $C_{1-6}$ alkyl, aryl, aryl $C_{1-6}$ alkyl, hetaryl (such as furanyl) or amino acid ester.

In preferred embodiments of the invention, formoterol fumarate (suitably as in the form of the dihydrate) is applied in combination with mometasone furoate (suitably as in the form of the monohydrate or more particularly in the anhydrous form).

Hereinafter, the term "formoterol" is understood to include formoterol or a pharmaceutical acceptable salt, solvate, or physiologically functional derivative thereof, preferably formoterol fumarate, while the term "mometasone" includes mometasone, or a pharmaceutical acceptable salt, solvate, or physiologically functional derivative thereof, preferably mometasone furoate, unless specified otherwise.

Formoterol and mometasone are generally present in a formulation of the invention in a therapeutically effective amount. The amount of formoterol and mometasone which is required to achieve a therapeutic effect will, of course, vary with the particular compound, the subject under treatment, and the particular disorder or disease being treated. Suitably, the pharmaceutical formulations which are suitable for inhalation according to the invention comprise formoterol and mometasone in amounts such that one or two actuations provide a therapeutically effective dose, for example, a dose of formoterol of 1 mcg to 50 mcg, preferably 3 mcg to 25 mcg, more preferably 4 mcg to 12 mcg and a dose of mometasone of 50 mcg to 1.6 mg, preferably 50 mcg to 1 mg, more preferably, 50 mcg to 200 mcg. Various dosing of the individual drugs can be advantageously combined for particular disorders or subjects under treatment. For example a formoterol dosing, such as 6 mcg per actuation can be combined with a low strength dosage of mometasone, e.g. 50 mcg per actuation, or a higher strength dosage, e.g. 200 mcg per actuation.

Preferably formoterol constitutes about 0.06 to about 0.60 mg per ml, more preferably about 0.08 to about 0.30 mg per ml, even more preferably about 0.1 to about 0.2 mg per ml, most preferably about 0.132 mg per ml of the formulation.

Mometasone preferably constitutes about 0.5 to about 15 mg per ml of the formulation. For high strength formulations mometasone constitutes preferably about 3 to about 15 mg per ml, more preferably about 4 to about 10 mg per ml, most preferably about 4.0 to 6.0 mg per ml of the formulation. For aerosol formulations including lower strength doses of mometasone, mometasone preferably constitutes about 0.5 to about 3.0 mg per ml, more preferably about 0.8 to about 2.5 mg per ml, most preferably about 1.00 to 1.25 mg per ml of the formulation.

The particles of formoterol or mometasone are generally micronised particles or particles processed by other methods, preferably having a mass median diameter equal to or greater than 1 micron, more particularly from 1 to 10 micron, even more particularly from 1 to 5 micron. Smaller particles having a mass median diameter of less than one micron may also be suitable.

The bulking agent having a mass median diameter of less than one micron, improves the stability of the suspension of formoterol and mometasone particles.

It is not necessary for the surface of the bulking agent or the drug to be coated with a surface modifier to achieve improved stability.

The mass median diameter of the bulking agent can advantageously be as low as 300 nanometers, more desirably as low as 250 nanometers, even more desirably the mass median diameter is in the range of 100 to 250 nanometers and most desirably in the range of 150 to 200 nanometers. In embodiments, the bulking agent has a mass median diameter of not more than 300 nanometers.

Mass median diameter (which is equivalent to volume median diameter) can be determined using any conventional particle size measurement method known to those skilled in the art. Suitable methods include for example laser diffraction, photon correlation spectroscopy (e.g. using a spectrometer available under the trade designation Brookhaven PCS from Brookhaven Inc.), spinning disc centrifuging (using an instrument available under the trade designation CPS Disc Centrifuge from Chemical Process Specialists Inc.) and scanning electron microscopy (SEM). Mass median diameter is preferably determined by laser diffraction, photon correlation spectroscopy or spinning disc centrifuging, more preferably by laser diffraction, more particularly laser diffraction using an analyser available under the trade designation Malvern Mastersizer 2000 laser light diffraction particle size analyser from Malvern Instruments Ltd.

Preferred bulking agents include lactose, DL-alanine, ascorbic acid, glucose, sucrose D(+)trehalose as well as their various hydrates, anomers and/or enantiomers. Lactose including its various forms, such as α-lactose monohydrate and β-lactose and alanine are more preferred. Lactose, in particular in its α-lactose monohydrate form, is most preferred as a bulking agent due to e.g. processing considerations. Other suitable bulking agents include other saccharides e.g. D-galactose, maltose, D(+)raffinose pentahydrate, sodium saccharin, polysaccharides e.g. starches, modified celluloses, dextrins or dextrans, other amino acids e.g. glycine, salts e.g. sodium chloride, calcium carbonate, sodium tartrate, calcium lactate, or other organic compounds e.g. urea or propyliodone.

Based on the amount of formoterol in the formulation, the weight ratio of formoterol to bulking agent is generally in the range 1:0.1 to 1:25, preferably 1:2 to 1:15, even more preferably 1:4 to 1:12 and most preferably 1:8 to 1:10.

For formulations including a low strength dosage of mometasone, e.g. 50 mcg per actuation, the weight ratio of total drug (formoterol and mometasone) to bulking agent is generally in the range 1:0.01 to 1:3, preferably 1:0.2 to 1:1.8, even more preferably 1:0.4 to 1:4 and most preferably about 1:0.94 to 1:1.17.

For formulations including a high strength dosage of mometasone, e.g. 200 mcg per actuation, the weight ratio of total drug (formoterol and mometasone) to bulking agent is generally in the range 1:0.002 to 1:6, preferably 1:0.05 to 1:0.4, even more preferably 1:0.1 to 1:3 and most preferably about 1:0.20 to 1:0.25.

To further enhance wetting characteristics of the formulation, and thus further minimizing the deposition of drug onto the metal parts of the container closure system and onto stainless steel manufacturing equipment during manufacture, the aerosol formulations of the invention may desirably contain ethanol. When ethanol is included in a formulation, it is generally present in an amount in the range 0.1 to 5% by weight of the total formulation, preferably from about 0.5 to about 4% by weight, more preferably from about 1 to about 3% by weight, most preferably about 2% by weight.

The aerosol formulations of the invention may preferably contain surfactant for e.g. imparting a flocculant effect which may allow less migration of the drugs to and from the metering chamber. When surfactant is included in a formulation it is generally present in an amount of about 0.001% to 0.050% by weight of the formulation. Suitable surfactants are well known in the art and include sorbitan trioleate, oleic acid and lecithin. Surfactants, such as oligolactic acid derivatives disclosed in WO94/21228 and WO94/21229, and other surfactants disclosed in the literature may be used. As a surfactant oleic acid is preferred.

The bulking agent may be reduced to the required particle size by any convenient method, e.g. grinding, air-jet milling etc. Preferably the bulking agent is reduced to nanoparticle size in a high pressure homogenizer, such as the commercially available Avestin Emulsiflex homogenizers and the Microfluidics Microfluidizer homogenizers. In the processing with high pressure homogenizers, certain bulking agents can be reduced to the desired particle size using lower pressures than that applied for other bulking agents. For example, it has been found that lactose, more specifically α-lactose monohydrate, can be effectively reduced to the desired particle size using pressures between about 10,000 and about 21,000 psi, while for effective particle size reduction of alanine or sucrose higher pressures of about 25,000 psi for repeated passes were applied.

The bulking agent may be prepared in a slurrying aid which is a low volatility solvent such as ethanol. It may be prepared in a slurrying aid which is a component of the final aerosol formulation, or it may be prepared in a solvent that is subsequently removed or exchanged with a component of the formulation by some process such as centrifugation and decanting, dialysis, evaporation etc.

It is particularly convenient to use a slurrying aid in the high pressure homogenizer which is a low volatility component of the aerosol formulation and after particle size reduction has been achieved the slurry may be adjusted if necessary, e.g. concentrated by centrifugation, decanting etc. Whilst it has been found that slurries with excessively high powder loadings may be difficult to process due to their rheological properties, it is generally advantageous to process slurries with powder loading concentrations which approach this processing limit in order to achieve the desired particle size distribution in the shortest processing time. Thus, the weight ratio of liquid:solid is generally in the range 5:1 to 100:1, preferably 5:1 to 20:1, and most preferably 8:1 to 10:1.

The present invention also provides a method of preparing a formulation according to the invention, the method comprising the steps of (i) forming a slurry of bulking agent with a component of the formulation; (ii) subjecting the slurry to high pressure homogenization; and (iii) combining the resulting slurry with other components of the aerosol formulation.

For formulations containing ethanol, the slurry of bulking agent may be advantageously prepared with an appropriate amount of ethanol. The slurry is subjected to high pressure homogenization prior to adding it to the remainder of the formulation. During manufacture, formoterol and mometasone are typically, initially dispersed with an appropriate amount of HFC 134a and/or HFC 227 and, if applicable or desired ethanol, i.e. such an amount of ethanol to aid dispersion but not so as to result in excessive partial solubilisation of either of the drugs, to prepare a cold concentrate. This dispersion, typically after high shear mixing, is then added to a second appropriate amount of HFC 134a and/or HFC 227 in liquid form, chilled to below its boiling point or range. Thereafter the (homogenized) bulking agent slurry is added. Alternatively the bulking agent slurry may be added to the second appropriate amount of propellant before the drug dispersion is added. If surfactant is used, it is preferably dissolved at ambient temperature in an appropriate amount of ethanol, and it is either added to the drug containing dispersion or the bulking agent slurry.

Alternatively, the formulations made by prepared by single stage or two stage pressure filling.

Dispensers comprising an aerosol vial equipped with conventional dispensing valves, preferably metered dose valves, can be used to deliver formulations of the invention. Conventional dispensers and aerosol vials can be used to contain a formulation of the invention. However it has been found that certain vials enhance the chemical stability of certain formulations of the invention. Therefore it is preferred to contain a formulation of the invention within a glass aerosol vial or a metal, in particular aluminum, vial having an interior surface coated with a polymer, in particular a fluorocarbon polymer. Advantageously other internal surfaces, in particular such surfaces of components of the valve, or all of the internal surfaces of the dispenser may be also coated with a polymer, in particular a fluorocarbon polymer. Suitable fluorocarbon polymers include fluorocarbon polymers, which are made of multiples of one or more of the following monomeric units: tetrafluoroethylene (PTFE), fluorinated ethylene propylene (FEP), perfluoroalkoxyalkane (PFA), ethylene tetrafluoroethylene (ETFE), vinylidenefluoride (PVDF), and chlorinated ethylene tetrafluoroethylene. Polymers, which have a relatively high ratio of fluorine to carbon, such as perfluorocarbon polymers e.g. PTFE, PFA, and FEP, are preferred; FEP is particularly preferred.

The valve may be any suitable metering valve with an outlet made from, for example, stainless steel, acetal, nylon or polybutylene terephthalate and with seals made from nitrile or EPDM elastomer.

A formulation of the invention can be administered to the lung by oral or nasal inhalation. Oral inhalation is preferred, and conventional actuators for oral inhalation can be used in connection with a formulation of the invention. It has been found that good respirable doses are achieved with an orifice diameter within the range of 0.4 to 0.6 mm, preferably in the range 0.45 to 0.55 mm, most preferably 0.47 to 0.53 mm.

The invention will be illustrated by the following Examples.

Materials Used:

α-lactose monohydrate supplied under the trade designation Pharmatose 325M by DMV International Pharma was micronised by fluid energy milling in a single pass (referred to here and in the following as "micronised lactose monohydrate"). Micronised lactose monohydrate (100 g) was dispersed in Anhydrous Ethanol (840 g) using a Silverson high shear mixer. This dispersion was added to the product reservoir of an Avestin Emulsiflex C50 homogenizer, and recirculated for 20 minutes at 10,000 psi. The dispersion was then passed out of the homogenizer, after recirculation for 30 seconds, at 20,000 psi. Two separate batches were prepared and their particle size determined.

DL-alanine (10 g, used as supplied by Fisher Chemicals, Loughborough UK) was dispersed in anhydrous ethanol (200 g) using a Silversen high shear mixer set at 10,000 RPM for 1 minute. The resultant dispersion was poured into the product vessel of a M110EH Microfluidizer. The Microfluidiser was fitted with an auxiliary process module of 100 micron channel diameter and a G10Z diamond interaction chamber of 87 micron channel diameter. The G10Z chamber was fitted downstream from the auxiliary process module. The dispersion was processed at 25,000 psi for 120 minutes.

Particle Size Analysis

For analysis of a Lactose/Ethanol slurry, a (0.5 ml) sample of the slurry, which was shaken for at least one minute to ensure homogeneity, was added to a solution of 0.05% Lecithin in Iso-octane (20 ml), and redispersed with mild ultrasonics for 1 minute.

The resulting suspension was introduced dropwise into the presentation cell (a Hydro 2000 SM small sample presentation cell) of a Malvern Mastersizer 2000™ laser diffraction particle sizer until the obscuration was in the working range (between 10 and 12 with a red laser), and left to circulate for 1 minute to allow complete mixing and thermal equilibrium to be established. Ten readings were taken at 20 second intervals to establish that the particle size was stable. The General Purpose analysis model, as described in the Malvern Instruments Operators Guide, was used with refractive indices 1.533 (lactose), 1.392 (iso-octane) and absorbance 0.001 (lactose). The results are based on the average calculated results of 10 readings taken in succession. The procedure was performed twice.

For analysis of Alanine, particle size analysis measurement was performed using a Malvern Mastersizer 2000™ laser diffraction particle sizer in an analogous manner to that described above for lactose, with the exception that a refractive index of 1.55 was employed for DL-alanine.

Results of Particle Size Analysis by Malvern Mastersizer 2000

| Units | Lactose Example 1 Microns | Lactose Example 2 Microns | DL-Alanine Example 3 Microns |
|---|---|---|---|
| d(v, 0.1) | 0.075 | 0.071 | 0.077 |
| d(v, 0.5) median | 0.181 | 0.160 | 0.190 |
| d(v, 0.9) | 0.896 | 0.793 | 0.600 |
| D[4, 3] volume weighted mean | 0.338 | 0.301 | 0.283 |

| Units | Percent | Percent | Percent |
|---|---|---|---|
| vol under 0.05 micron | 1.85 | 2.20 | 1.68 |
| vol under 0.10 micron | 20.78 | 24.35 | 19.13 |
| vol under 0.20 micron | 54.71 | 61.09 | 52.45 |
| vol under 0.50 micron | 81.33 | 82.53 | 86.56 |
| vol under 1.0 micron | 91.65 | 93.55 | 96.25 |
| vol under 2.0 micron | 99.38 | 99.84 | 99.98 |
| vol under 5.0 micron | 100.0 | 100.00 | 100.00 |
| vol under 10.0 micron | 100.00 | 100.00 | 100.00 |
| vol under 20.0 micron | 100.00 | 100.00 | 100.00 |

Exemplary Formulations

Examples 4-15

Each formulation was prepared in a PET vial. The appropriate amounts of micronised drugs, a racemic mixture of formoterol fumarate dihydrate and mometasone furoate, were weighed into the PET vial. A slurry of nanosized lactose in ethanol from Example 1 was added as a thick paste to the PET vial; but initially not allowed to mix with the powdered drugs. A propellant mixture was prepared in a separate aerosol can, containing the propellant and the balance of any other ingredients in proportion that had not already been added. A non-metering valve was crimped onto the PET vial, which was then charged with the prescribed weight of propellant mixture from the aerosol can to prepare formulations by mixing all the ingredients. These were further mixed for 1 minute in an ultrasonic bath.

Comparative formulations A-D without lactose were prepared as follows. Each formulation was prepared in a PET vial. The appropriate amounts of micronised drugs were weighed into the PET vial. A propellant mixture was prepared in a separate aerosol can, containing the propellant and the balance of any other ingredients in proportion that had not already been added (ie. a higher ethanol mix than that used for the examples of the invention). A non-metering valve was crimped onto the PET vial, which was then charged with the prescribed weight of propellant mixture from the aerosol can to prepare formulations by mixing all the ingredients. These were further mixed for 1 minute in an ultrasonic bath.

The physical characteristics and suspension settling rates of prepared formulations were examined by shaking the formulation and observing the formulation upon standing visually and by using an optical measuring technique such as that described in the Proceedings of Drug Delivery to the Lung VI p. 10-13 (December 1995) printed by the Aerosol Society. To use such equipment, a PET vial containing a unit quantity of formulation was placed on a vortex mixer for 10 seconds and then immediately placed into the test apparatus. The apparatus was set up with an upper light beam and detector 3 mm below the liquid meniscus and a lower light beam and detector 3 mm above the base of the vial. It was also set up to automatically start recording the light transmission to each detector as the vial passed the upper beam upon insertion. The transmission was captured as a plot of voltage against time. For sedimenting formulations the data from the upper sensor were used.

HFC 134a-Based Formulations

| | \multicolumn{4}{c}{Formulation no.} | | | |
|---|---|---|---|---|
| | mg/ml | g/unit | mg/ml | g/unit |
| | A | | 4 | |
| Formoterol fumarate | 0.1320 | 0.0010 | 0.1320 | 0.0010 |
| Mometasone furoate | 1.0000 | 0.0083 | 1.0000 | 0.0083 |
| Lactose monohydrate | 0.0000 | 0.0000 | 1.3200 | 0.0109 |
| Oleic Acid | 0.0606 | 0.0005 | 0.0606 | 0.0005 |
| Ethanol | 24.2200 | 0.2000 | 24.2200 | 0.2000 |
| HFA 134a | 1185.5874 | 9.7902 | 1184.2674 | 9.7793 |
| | 5 | | 6 | |
| Formoterol fumarate | 0.1320 | 0.0010 | 0.1320 | 0.0010 |
| Mometasone furoate | 1.0000 | 0.0083 | 1.0000 | 0.0083 |
| Lactose monohydrate | 1.9800 | 0.0164 | 2.6400 | 0.0218 |
| Oleic Acid | 0.0606 | 0.0005 | 0.0606 | 0.0005 |
| Ethanol | 24.2200 | 0.2000 | 24.2200 | 0.2000 |
| HFA 134a | 1183.6074 | 9.7738 | 1182.9474 | 9.7684 |
| | B | | 7 | |
| Formoterol fumarate | 0.1320 | 0.0010 | 0.1320 | 0.0010 |
| Mometasone furoate | 5.0000 | 0.0413 | 5.0000 | 0.0413 |
| Lactose monohydrate | 0.0000 | 0.0000 | 1.3200 | 0.0109 |
| Oleic Acid | 0.0606 | 0.0005 | 0.0606 | 0.0005 |
| Ethanol | 24.2200 | 0.2000 | 24.2200 | 0.2000 |
| HFA 134a | 1181.5874 | 9.7572 | 1180.2674 | 9.7463 |
| | 8 | | 9 | |
| Formoterol fumarate | 0.1320 | 0.0010 | 0.1320 | 0.0010 |
| Mometasone furoate | 5.0000 | 0.0413 | 5.0000 | 0.0413 |
| Lactose monohydrate | 1.9800 | 0.0164 | 2.6400 | 0.0218 |
| Oleic Acid | 0.0606 | 0.0005 | 0.0606 | 0.0005 |
| Ethanol | 24.2200 | 0.2000 | 24.2200 | 0.2000 |
| HFA 134a | 1179.6074 | 9.7408 | 1178.9474 | 9.7354 |

The formulations containing nano-sized lactose show better physical stability over the comparative formulations. All the formulations containing nano-sized lactose exhibited a significant slower rate of sedimentation than the lactose-free formulations. After standing 15 minutes it was noted that the sediment volume of the nano-sized lactose formulations 4-6 occupied approximately 35 to 55% of the formulation volume, while the non-bulked formulations showed a sediment occupying about 20% of the total formulation volume.

A preparation of Formulation 6 was also carried out using the lab scale process described below for Formulation 16, and defined portions thereof were cold-transferred to the following container-closure systems:

P Plain aluminium canister with a 50 mcl Spraymiser™ valve crimped.

Q Aluminium canister lined with Fluorinated Ethylene Propylene polymeric coating, with a 50 mcl Spraymiser™ valve crimped.

Two of each of P and Q canisters were left to equilibrate at room temperature for 24 hours, then stored for 5 days at 50° C. in a valve-down orientation, then allowed to equilibrate for 24 hours at room temperature prior to analysis. A High Pressure Liquid Chromatographic analysis of the canister contents was performed to assess the levels of impurities, with the following average results:

|             | P    | Q    |
| ----------- | ---- | ---- |
| % impurities | 1.26 | 0.98 |

The experiment showed that lining the internal surface of the canister with a fluorocarbon polymeric coating reduced the level of degradation significantly.

HFC 227-Based Formulations

|                    | Formulation no. | | | |
| --- | --- | --- | --- | --- |
|                    | mg/ml    | g/unit  | mg/ml    | g/unit  |
|                    | C        |         | 10       |         |
| Formoterol fumarate | 0.1320   | 0.0009  | 0.1320   | 0.0009  |
| Mometasone furoate  | 1.0000   | 0.0072  | 1.0000   | 0.0072  |
| Lactose monohydrate | 0.0000   | 0.0000  | 1.3200   | 0.0095  |
| Oleic Acid          | 0.0695   | 0.0005  | 0.0695   | 0.0005  |
| Ethanol             | 27.8000  | 0.2000  | 27.8000  | 0.2000  |
| HFA 227             | 1360.9985| 9.7914  | 1359.6785| 9.7819  |
|                    | 11       |         | 12       |         |
| Formoterol fumarate | 0.1320   | 0.0009  | 0.1320   | 0.0009  |
| Mometasone furoate  | 1.0000   | 0.0072  | 1.0000   | 0.0072  |
| Lactose monohydrate | 1.9800   | 0.0143  | 2.6400   | 0.0190  |
| Oleic Acid          | 0.0695   | 0.0005  | 0.0695   | 0.0005  |
| Ethanol             | 27.8000  | 0.2000  | 27.8000  | 0.2000  |
| HFA 227             | 1359.0185| 9.7771  | 1358.3585| 9.7724  |
|                    | D        |         | 13       |         |
| Formoterol fumarate | 0.1320   | 0.0009  | 0.1320   | 0.0009  |
| Mometasone furoate  | 5.0000   | 0.0360  | 5.0000   | 0.0360  |
| Lactose monohydrate | 0.0000   | 0.0000  | 1.3200   | 0.0095  |
| Oleic Acid          | 0.0695   | 0.0005  | 0.0695   | 0.0005  |
| Ethanol             | 27.8000  | 0.2000  | 27.8000  | 0.2000  |
| HFA 227             | 1356.9985| 9.7626  | 1355.6785| 9.7531  |
|                    | 14       |         | 15       |         |
| Formoterol fumarate | 0.1320   | 0.0009  | 0.1320   | 0.0009  |
| Mometasone furoate  | 5.0000   | 0.0360  | 5.0000   | 0.0360  |
| Lactose monohydrate | 1.9800   | 0.0143  | 2.6400   | 0.0190  |
| Oleic Acid          | 0.0695   | 0.0005  | 0.0695   | 0.0005  |
| Ethanol             | 27.8000  | 0.2000  | 27.8000  | 0.2000  |
| HFA 227             | 1355.0185| 9.7483  | 1354.3585| 9.7436  |

The formulations without lactose exhibited a tendency to cream. The formulations containing nano-sized lactose exhibited superior physical stability properties, no creaming and a slow sedimentation rate. After standing 15 minutes it was noted that the sediment volume of the nano-sized lactose formulations occupied greater than 50% of the formulation volume, while the non-bulked formulations had nebulous flocs in which more than half of the flocs creamed and others floated in the formulation without filling any particular region of the formulation volume. It was also observed that the sedimentation rate for the nano-bulked HFC 227 based formulations was slower than the corresponding formulations using HFC 134a.

These examples demonstrate that the use of a nano-sized bulking agent enhances the physical stability of dispersed formoterol and mometasone particles.

Exemplary Formulation 16

A Lab scale preparation of each formulation was carried out to make 100 inhalers as follows. Oleic acid was weighed into a stainless steel beaker, followed by a quantity of the slurry of lactose with ethanol (from Example 2). Finally, the balance of ethanol was added and the mixture stirred with a spatula to ensure complete mixing. Each micronized drug, a racemic mixture of formoterol fumarate dihydrate and mometasone furoate, was weighed into another stainless steel beaker. The 2 beakers were transferred to the dehumidified atmosphere of a cold filler. About 250 grams of propellant were added to the excipients beaker to wash into the batching vessel. The remainder of the propellant required for the formulation was added to the batching vessel. The drugs were tipped from their beaker into the batching vessel, and a high shear mixer lowered in to mix all the ingredients at 8000 rpm for two minutes. A magnetic flea was added to the batching vessel to allow continued mixing while the batch was transferred to aerosol canisters.

|                     | Formulation no. | |
| --- | --- | --- |
|                     | mg/ml     | g/unit  |
|                     | 16        |         |
| Formoterol fumarate | 0.1320    | 0.0010  |
| Mometasone furoate  | 1.2500    | 0.0103  |
| Lactose monohydrate | 1.3200    | 0.0109  |
| Oleic Acid          | 0.0606    | 0.0005  |
| Ethanol             | 24.2200   | 0.2000  |
| HFA 134a            | 1184.0174 | 9.7773  |

Formulation 16 was transferred into 10 ml aluminium canisters and crimped with 50 microliter Spraymiser™ valves.

Test Methods

Uniformity of Content

The aerosol units to be tested were inserted sequentially into a single standard actuator. Each inhaler so assembled was shaken with a gentle rolling action through 180 degrees inversion at 1 cycle per second for 4 seconds. Within 2 seconds a single shot was fired to waste by pressing the unit down for 1 second, then the inhaler allowed to stand for 30 seconds. This process was repeated to fire 10 "priming" shots to waste.

The apparatus described and illustrated in European Pharmacopoeia $3^{rd}$ edition 2001 Supplement pages S1658-9 with a grommet to seal the actuator to the apparatus was used to collect shots fired for assay. Each inhaler was actuated using the same actuation protocol as used for the priming shots. 5 seconds after actuation, the pump was switched off and the inhaler removed. The apparatus (with filter) and grommet were quantitatively rinsed with 10 ml of sample diluent (methanol:acetonitrile:water in the ratio 1:1:1) by sealing the 2 ends of the apparatus, shaking for 30 seconds, placing in an ultrasonic bath for 1 minute and shaking for a further 30 seconds. The sample diluent was then analysed by High Pressure Liquid Chromatography to determine the content of both drugs. This method was used to assay the content of shots 11-16 (start), 59-62 (middle) and 118-120 (end) of each unit tested.

Loss of Dose

The loss of dose was determined by applying the method for content analysis above.

The protocol was as follows.

After collecting dose 16, each inhaler was left to stand for 24 hours in a valve-up orientation. Then without priming, shots 17 and 18 were analysed in the same way as shots 15 and 16. For the double shot values tabulated, 2 consecutive shots taken 24 hours after the previous dispensed dose were compared with shots 15 and 16, the values corresponding to the mean of shots 17 and 18 represented as a percentage of the mean of shots 15 and 16. The single shot values compared shot 17 with the mean of shots 15 and 16.

Andersen Particle Size

The Andersen sampler (Apparatus 1, US Pharmacopoeia 24 monograph <601>) was used as follows. A filter paper (Whatman 934-AH) was cut to fit the "F" stage, which was incorporated into the stack. The remainder of the stack was assembled, including the USP throat.

Each unit was tested as follows.

Priming shots (10) were fired through a standard actuator as described in the method for uniformity of content. The valve and valve stem interior were cleaned with water (30 ml) followed by ethanol (30 ml) and dried thoroughly. The unit was weighed. An unused sample actuator was used to dispense doses while the Andersen sampler was drawing air at 28.3 liter per minute. This was kept sealed into the port of the USP throat with a grommet until 5 seconds after actuation. 20 shots were fired, using the actuation protocol described for uniformity of content. The vacuum source was switched off 30 seconds after the final actuation. The unit was weighed.

The valve stem (including the interior), actuator, throat (including grommet), Stage 0 and inlet cone, plates 0-2, plates 3-5, plates 6-7 and the filter were separately rinsed with the following diluents:

| Parts | Diluent |
| --- | --- |
| Valve stem | Acetonitrile (20 ml), methanol (20 ml), water (20 ml), sequentially |
| Actuator | |
| Throat and grommet | Acetonitrile (30 ml), methanol (30 ml), water (30 ml), sequentially |
| Stage 0 and inlet cone | Sample diluent (10 ml) |
| Plates 0-2 | |
| Plates 3-5 | Sample diluent (50 ml) |
| Plates 6-7 | Sample diluent (10 ml) |
| Filter | Acetonitrile (3 ml), methanol (3 ml), water (3 ml), sequentially |

The sample diluent was as used for uniformity of content

Each washing was analysed by High Pressure Liquid Chromatography to determine each drug content in micrograms.

The calculation of parameters tabulated is as follows.

Fine particle fraction =

$$\frac{\text{drug analysed from plates 3 to 7 and the filter (microgams)}}{\text{Drug analysed from the throat, grommet, Stage 0, inlet cone, Plates 0 to 7 and the filter (micrograms)}} \times 100\%$$

Fine particle dose = drug analysed from plates 3 to 7 and the filter (microgams)

Mean metered dose = total recovery of drug from all diluent samples (micrograms)

Results

Uniformity of Content (Start, Middle and End)

Dose dispensed per shot ex actuator in micrograms and relative standard deviation expressed as %

| Micrograms per actuation | | Start | Middle | End |
| --- | --- | --- | --- | --- |
| Formoterol fumarate | mcg/actuation | 5.5 | 6.2 | 5.8 |
| | RSD % | 5.4 | 6.0 | 5.0 |
| Mometasone furoate | mcg/actuation | 53.2 | 55.4 | 54.5 |
| | RSD % | 6.1 | 5.4 | 3.7 |

The uniformity of content is satisfactory.

Loss of Dose Test (% Dispensed After 24 Hours Standing Compared with 0 Hours)

| | | % |
| --- | --- | --- |
| Formoterol fumarate | Single shot | 101.5 |
| | Double shot | 106.0 |
| Mometasone furoate | Single shot | 95.5 |
| | Double shot | 99.1 |

The formulation has performed well after standing for a 24 hour period.

Andersen Particle Size

| | Formoterol fumarate | Mometasone furoate |
| --- | --- | --- |
| Mean fine particle fraction (%) | 39.4 | 40.7 |
| Fine particle dose (micrograms per shot) | 2.3 | 21.6 |
| Mean metered shot (micrograms) | 7.3 | 66.4 |

Formulations 17 and 18

These formulations were prepared as described under the heading Formulation 16.

| | Formulation no. | | | | | |
| --- | --- | --- | --- | --- | --- | --- |
| | E | | 17 | | 18 | |
| | mg/ml | g/unit | mg/ml | g/unit | mg/ml | g/unit |
| Formoterol fumarate | 0.1320 | 0.0009 | 0.1320 | 0.0009 | 0.1320 | 0.0009 |
| Mometasone furoate | 1.2500 | 0.0090 | 1.2500 | 0.0090 | 5.0000 | 0.0360 |
| Lactose monohydrate | 0.0000 | 0.0000 | 1.3200 | 0.0095 | 1.3200 | 0.0095 |
| Oleic Acid | 0.0695 | 0.0005 | 0.0695 | 0.0005 | 0.0695 | 0.0005 |
| Ethanol | 27.8000 | 0.2000 | 27.8000 | 0.2000 | 27.8000 | 0.2000 |
| HFA 227 | 1359.4285 | 9.7801 | 1360.7485 | 9.7896 | 1355.6785 | 9.7531 |

Formulations 17, 18 and E were transferred into 10 ml FEP-lined aluminium canisters and crimped with 50 microliter valves incorporating a thermoplastic elastomer gasket to prevent contact between the formulation and aluminium surfaces, as described and shown in FIG. 1 of U.S. Pat. No. 6,264,923 B1.

Results

Loss of Dose Test (% Dispensed After 24 Hours Standing Compared with 0 Hours)

|  |  | Formulation | | |
|---|---|---|---|---|
| % |  | E | 17 | 18 |
| Formoterol fumarate | Single shot | 82.2 | 101.1 | 94.6 |
|  | Double shot | 96.1 | 106.8 | 97.2 |
| Mometasone furoate | Single shot | 84.0 | 99.5 | 98.9 |
|  | Double shot | 98.1 | 104.0 | 100.9 |

The loss of dose for formulations 17 and 18 was far superior to that for the comparative formulation E.

Andersen Particle Size

|  | Formulation | | | |
|---|---|---|---|---|
|  | 17 | | 18 | |
|  | Formoterol fumarate | Mometasone furoate | Formoterol fumarate | Mometasone furoate |
| Mean fine particle fraction (%) | 47.1 | 47.6 | 40.2 | 43.0 |
| Fine particle dose (micrograms per shot) | 2.6 | 24.6 | 2.2 | 87.6 |
| Mean metered shot (micrograms) | 6.8 | 62.5 | 6.6 | 248.5 |

The Andersen particle size results represent reasonable delivery from the formulations.

Examples 19 and 20

A formulation according to Formulation 16 was prepared and defined portions were transferred to PET vials, which were subsequently crimped with a non-metering valve, in a similar manner as that described for Examples 4-15. This formulation is designated as Formulation 19. Formulation 20 was prepared in the same way as formulation 16, but with Alanine (from Example 3) substituted for Lactose. A comparative formulation, Formulation F was prepared similarly to formulation E. Corresponding portions of these formulations were also transferred to PET vials. The prepared formulations were then examined visually and by using an optical measuring technique as described above for Examples 4-15.

|  | Formulation no. | | | | | |
|---|---|---|---|---|---|---|
|  | F | | 19 | | 20 | |
|  | mg/ml | g/unit | mg/ml | g/unit | mg/ml | g/unit |
| Formoterol fumarate | 0.1320 | 0.0010 | 0.1320 | 0.0010 | 0.1320 | 0.0010 |
| Mometasone furoate | 1.2500 | 0.0103 | 1.2500 | 0.0103 | 1.2500 | 0.0103 |
| Lactose monohydrate | 0.0000 | 0.0000 | 1.3200 | 0.0109 | 0.0000 | 0.0000 |
| Alanine | 0.0000 | 0.0000 | 0.0000 | 0.0000 | 1.2300 | 0.0101 |
| Oleic Acid | 0.0606 | 0.0005 | 0.0606 | 0.0005 | 0.0606 | 0.0005 |
| Ethanol | 24.2200 | 0.2000 | 24.2200 | 0.2000 | 24.2200 | 0.2000 |
| HFA 134a | 1185.3374 | 9.7882 | 1184.0174 | 9.7781 | 1184.0174 | 9.7781 |

Formulation 19 showed a significantly slower settling rate than comparative formulation F, while surprisingly Formulation 20 sedimented even more slowly than Formulation 19. After standing 15 minutes it was noted that the sediment volume of the nano-sized lactose and alanine formulations occupied approximately 30% and 23% respectively of the formulation volume, while the non-bulked formulation showed a sediment occupying about 7% of the total formulation volume.

The invention claimed is:

1. A dispenser comprising an aerosol vial equipped with a dispensing valve, said aerosol vial containing a pharmaceutical aerosol formulation comprising particles of (a) formoterol fumarate dihydrate and (b) mometasone furoate dispersed in a propellant selected from the group consisting of 1,1,1,2-tetrafluoroethane, 1,1,1,2,3,3,3-heptafluoropropane and a mixture thereof, and a bulking agent having a mass median diameter of not more than 300 nanometers.

2. A pharmaceutical aerosol formulation according to claim 1, wherein the formoterol is present in an amount of about 0.06 to 0.60 mg per ml.

3. A pharmaceutical aerosol formulation according to claim 1, wherein the mometasone is present in amount of about 0.5 to 15.0 mg per ml.

4. A pharmaceutical aerosol formulation according to claim 1, wherein the bulking agent is selected from groups consisting of ascorbic acid, saccharides, polysaccharides, amino acids, organic and inorganic salts, urea and propyliodone.

5. A pharmaceutical aerosol formulation according to claim 4, wherein the bulking agent is selected from lactose, DL-alanine, glucose, D-galactose, D(+)trehalose dihydrate, sucrose, maltose, D(+)raffinose pentahydrate, sodium saccharin, starches, modified celluloses, dextrins, dextrans, glycine, sodium chloride, calcium carbonate, sodium tartrate and calcium lactate.

6. A pharmaceutical aerosol formulation according to claim 4, wherein the bulking agent is lactose.

7. A pharmaceutical aerosol formulation according to claim 1, wherein the weight ratio of formoterol to bulking agent is in the range 1:0.1 to 1:30.

8. A pharmaceutical aerosol formulation according to claim 1, wherein the bulking agent has a mass median diameter in a range from 100 to 250 nanometers.

9. A pharmaceutical aerosol formulation according to claim 1, wherein the formulation further comprises a surfactant.

10. A pharmaceutical aerosol formulation according to claim 1, wherein the formulation further comprises ethanol.

11. A pharmaceutical aerosol formulation according to claim 10, wherein ethanol is present in amount of from 0.1 to 5% by weight of the formulation.

12. A method of preparing a formulation according to claim 1, the method comprising the steps of (i) forming a slurry of bulking agent with a component of the formulation; (ii) subjecting the slurry to high pressure homogenization; and (iii) combining the resulting slurry with other components of the aerosol formulation.

* * * * *